(12) United States Patent
Huang et al.

(10) Patent No.: US 12,016,681 B2
(45) Date of Patent: Jun. 25, 2024

(54) PHYSIOLOGICAL SIGNAL MONITORING DEVICE AND ASSEMBLING METHOD OF A TRANSMITTER THEREOF

(71) Applicant: BIONIME CORPORATION, Taichung (TW)

(72) Inventors: Chun-Mu Huang, Taichung (TW); Chieh-Hsing Chen, Taichung (TW)

(73) Assignee: BIONIME CORPORATION, Taichung (TW)

( * ) Notice: Subject to any disclaimer, the term of this patent is extended or adjusted under 35 U.S.C. 154(b) by 239 days.

(21) Appl. No.: 16/983,198

(22) Filed: Aug. 3, 2020

(65) Prior Publication Data

US 2021/0030332 A1 Feb. 4, 2021

Related U.S. Application Data

(60) Provisional application No. 62/882,140, filed on Aug. 2, 2019.

(51) Int. Cl.
*A61B 5/145* (2006.01)
*A61B 5/00* (2006.01)
(Continued)

(52) U.S. Cl.
CPC ........ *A61B 5/14503* (2013.01); *A61B 5/0002* (2013.01); *A61B 5/0004* (2013.01);
(Continued)

(58) Field of Classification Search
CPC ............ A61B 5/14503; A61B 5/14532; A61B 5/6801; A61B 2562/166; A61B 2562/227; A61B 5/0002; A61B 5/0004; A61B 5/14546; A61B 5/14865; A61B 5/6849; A61B 5/6867; A61B 5/688; A61B 5/1451;
(Continued)

(56) References Cited

U.S. PATENT DOCUMENTS 6,589,229 B1 7/2003 Connelly et al.
2017/0290533 A1* 10/2017 Antonio ............. A61B 5/14532
(Continued)

FOREIGN PATENT DOCUMENTS

WO 2013090215 A2 6/2013
WO 2013152090 A2 10/2013
(Continued)

OTHER PUBLICATIONS

Search Report issued to European counterpart application No. 20189233.8 by the EPO dated Nov. 24, 2020.

*Primary Examiner* — Jay B Shah
*Assistant Examiner* — Meghan R Kumar
(74) *Attorney, Agent, or Firm* — Perkins Coie LLP; Sean Lee; Viola Kung (57) ABSTRACT

A physiological signal monitoring device includes a biosensor, and a transmitter including a bottom casing, a processing unit and a battery. The bottom casing has a first stepped section, a second stepped section, and a riser section interconnecting the first stepped section and the second stepped section. The processing unit corresponds in position to the first stepped section. The battery corresponds in position to the first stepped section, and is configured not to overlap the processing unit in a direction of a first axis so as to reduce a thickness of the transmitter.

18 Claims, 10 Drawing Sheets

(51) Int. Cl.
*A61B 5/1486* (2006.01)
*H01R 12/73* (2011.01)

(52) U.S. Cl.
CPC ...... *A61B 5/14532* (2013.01); *A61B 5/14546* (2013.01); *A61B 5/14865* (2013.01); *A61B 5/6801* (2013.01); *A61B 5/6849* (2013.01); *A61B 5/6867* (2013.01); *A61B 5/688* (2013.01); *A61B 5/1451* (2013.01); *A61B 2560/045* (2013.01); *A61B 2560/063* (2013.01); *A61B 2562/0295* (2013.01); *A61B 2562/14* (2013.01); *A61B 2562/16* (2013.01); *A61B 2562/166* (2013.01); *A61B 2562/168* (2013.01); *A61B 2562/225* (2013.01); *A61B 2562/226* (2013.01); *A61B 2562/227* (2013.01); *H01R 12/737* (2013.01)

(58) Field of Classification Search
CPC ........ A61B 2560/045; A61B 2560/063; A61B 2562/0295; A61B 2562/14; A61B 2562/16; A61B 2562/168; A61B 2562/225; A61B 2562/226; A61B 2562/242; A61B 2562/164; A61B 5/150748; A61B 5/150847; A61B 5/6833; H01R 12/737

See application file for complete search history.

(56) References Cited

U.S. PATENT DOCUMENTS

2017/0290546 A1\* 10/2017 Antonio ............... A61B 5/1473
2018/0116572 A1\* 5/2018 Simpson ................ A61B 5/683

FOREIGN PATENT DOCUMENTS

| WO | 2016036924 A2 | 3/2016 | |
|---|---|---|---|
| WO | 2017116915 A1 | 7/2017 | |
| WO | WO-2017116915 A1 \* | 7/2017 | ......... A61B 5/14503 |

\* cited by examiner

PHYSIOLOGICAL SIGNAL MONITORING DEVICE AND ASSEMBLING METHOD OF A TRANSMITTER THEREOF

CROSS-REFERENCE TO RELATED APPLICATION

This application claims priority of U.S. Provisional Patent Application No. 62/882,140, filed on Aug. 2, 2019.

FIELD

The disclosure relates to a sensing device, and more particularly to a physiological signal monitoring device and an assembling method of a transmitter thereof.

BACKGROUND

Continuous glucose monitoring (GCM) is a popular method for tracking changes in blood glucose levels by taking glucose measurements of an individual at regular intervals. In order to utilize a CGM system, the individual needs to wear a sensing device, which at least includes a biosensor for sensing physiological signal corresponding to the glucose level of a host, and a transmitter for receiving and transmitting the abovementioned physiological signal for a period. In order to prevent the device from being detached by any accidental collision during the period, a compact, miniature sensing device with reduced thickness is necessary. In the meanwhile, the structural stability and fluid-tightness of a miniaturized transmitter may not meet the practical requirements.

SUMMARY

Therefore, an object of the disclosure is to provide a physiological signal monitoring device that can alleviate the drawback of the prior art.

According to the disclosure, the physiological signal monitoring device is adapted for measuring at least one physiological parameter of a host, and includes a biosensor and a transmitter. The biosensor is adapted to be partially inserted underneath a skin surface of the host for measuring and sending a physiological signal corresponding to the physiological parameter. The transmitter is coupled to the biosensor in a direction of a first axis, and includes a bottom casing that has at least one first stepped section, a second stepped section, and a riser section interconnecting the first stepped section and the second stepped section, wherein the first stepped section and the second stepped section are spaced apart from each other in the direction of the first axis, a top casing that seals the bottom casing and that cooperates with the bottom casing to define an inner space therebetween, a circuit board that is located in the inner space, that at least abuts against the second stepped section, and that extends toward the first stepped section, a processing unit that is disposed on the circuit board and that corresponds in position to the first stepped section for processing the physiological signal, a battery that is located in the inner space and that is electrically coupled to the circuit board, wherein the battery corresponds in position to the first stepped section, and is configured not to overlap the processing unit in the direction of the first axis so as to reduce a thickness of the transmitter in the direction of the first axis, and a connecting port that is disposed on the second stepped section and that permits the biosensor to be coupled to the circuit board for sending the physiological signal to the processing unit.

Another object of the disclosure is to provide an assembling method of a transmitter of the physiological signal monitoring device that can alleviate the drawback of the prior art.

According to the disclosure, the assembling method includes steps of: A) adhering a portion of the circuit board to the second stepped section of the bottom casing in the direction of the first axis to allow the processing unit and the battery that are connected to the circuit board to correspond in position to the first stepped section; B) moving the top casing to face the bottom casing in the direction of the first axis, and coupling the top casing to the bottom casing such that the circuit board, the battery and the processing unit are located in the inner space cooperatively defined by the top casing and the bottom casing; and C) the bottom casing further having a through hole that communicates the inner space with an external environment, pouring a curing agent into the inner space via the through hole of the bottom casing such that the bottom casing and the top casing are coupled to each other, that the circuit board, the battery and the processing unit are fixedly positioned relative to each other, and that the inner space is sealed.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Before the disclosure is described in greater detail, it should be noted that where considered appropriate, reference numerals or terminal portions of reference numerals have been repeated among the figures to indicate corresponding or analogous elements, which may optionally have similar characteristics.

In addition, in the description of the disclosure, the terms "up", "down", "top", "bottom" are meant to indicate relative position between the elements of the disclosure, and are not meant to indicate the actual position of each of the elements in actual implementations. Similarly, various axes to be disclosed herein, while defined to be perpendicular to one another in the disclosure, may not be necessarily perpendicular in actual implementation.

Figure 1:
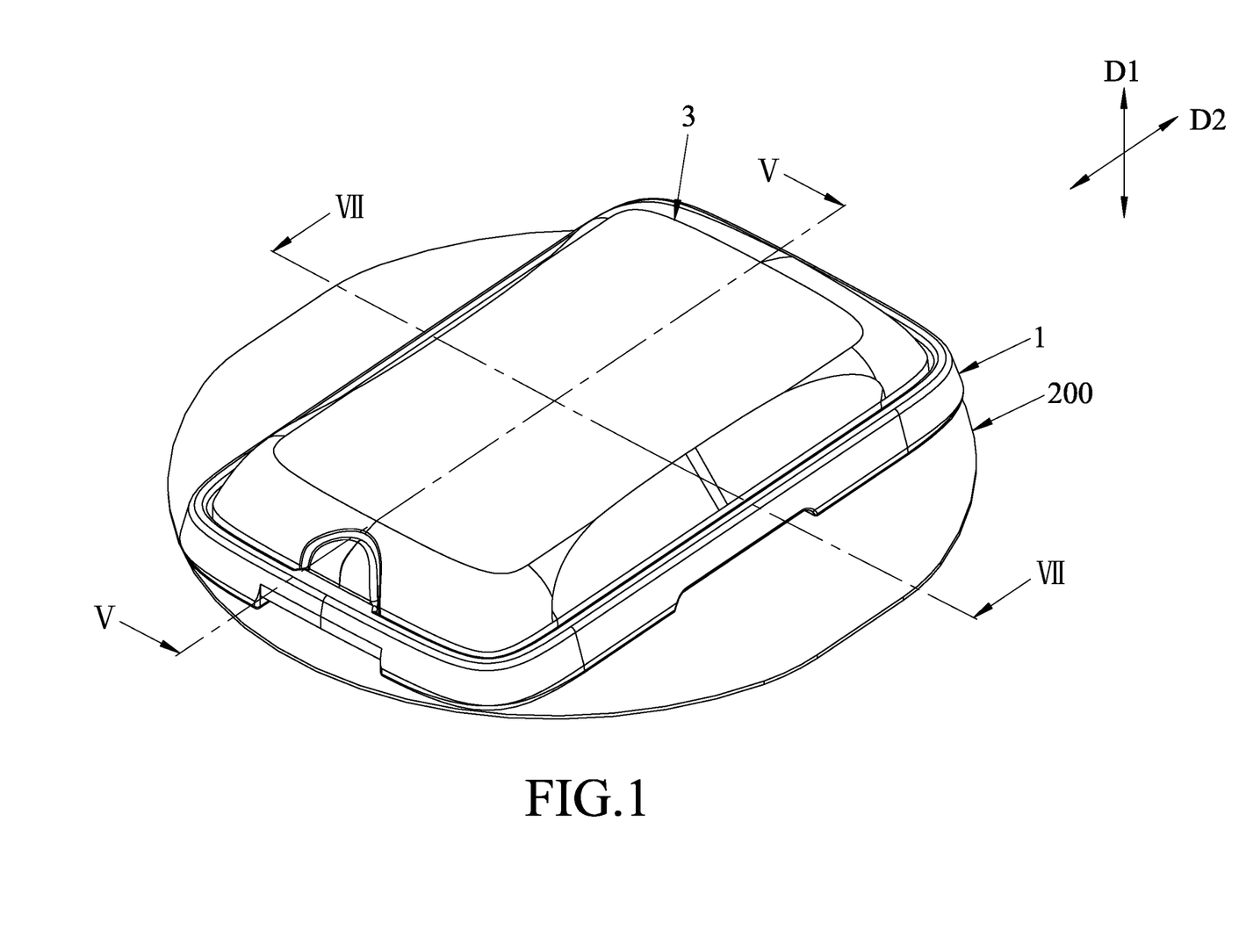
FIG. 1 is a perspective view of a first embodiment of the physiological signal monitoring device according to the disclosure.
Figure 2:
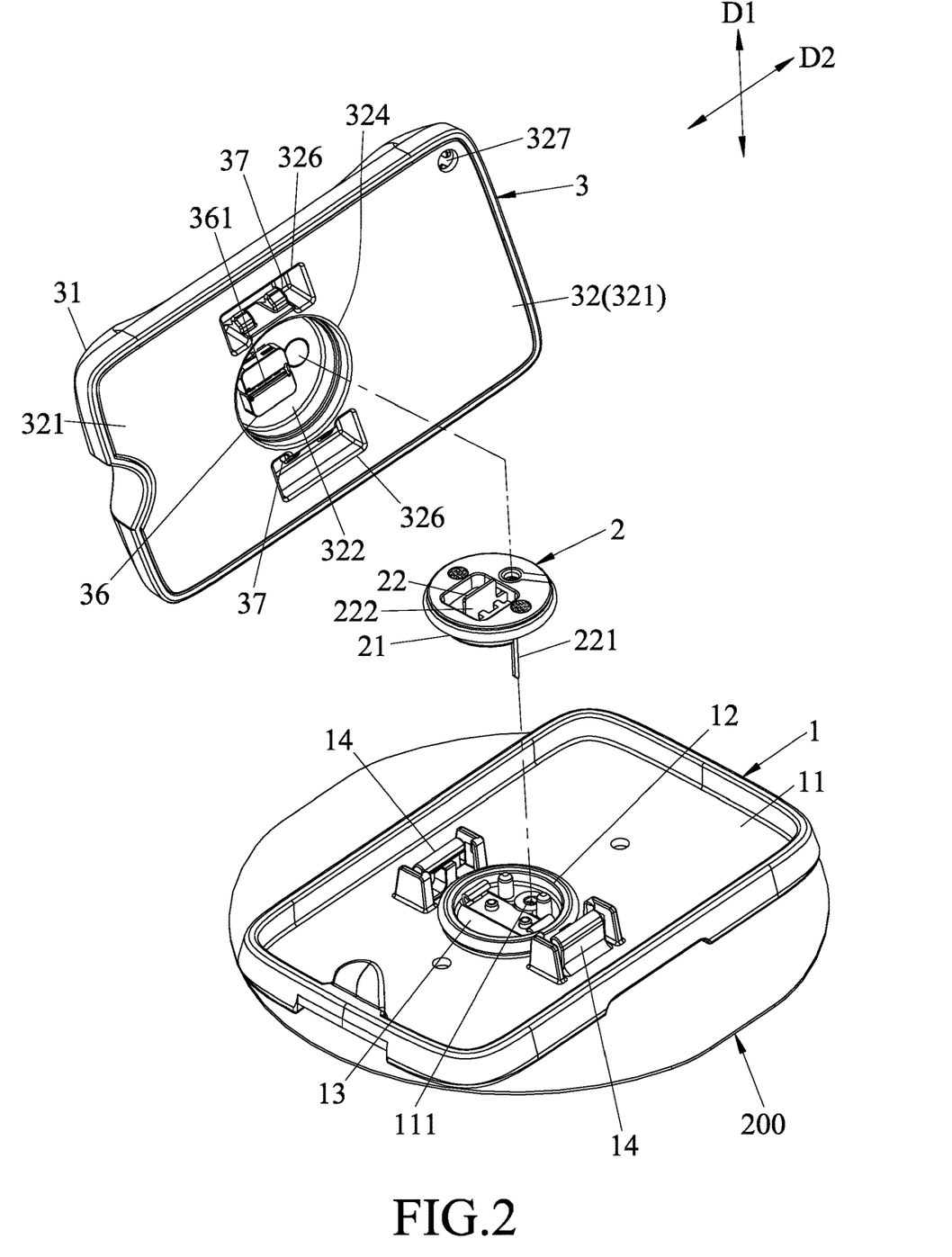
FIG. 2 is an exploded perspective view illustrating the first embodiment.

Referring to FIGS. 1 and 2, a first embodiment of the physiological signal monitoring device according to the disclosure is adapted to be mounted to a skin surface of a host (not shown), and is adapted for measuring at least one physiological parameter of an analyte of the host and for transmitting a corresponding physiological signal. In this embodiment, the physiological signal monitoring device is for measuring the blood glucose concentration in the interstitial fluid (ISF) of the host, but is not restricted to such.

The physiological signal monitoring device includes abase 1 that is adapted to be mounted to the skin surface of the host, a biosensor 2 that is mounted to the base and that is adapted to be partially inserted underneath the skin surface of the host, and a transmitter 3 that is removably covered to the base 1 in a direction of a first axis (D1) and that is connected to the biosensor 2. The biosensor 2 is adapted for measuring the analyte of the host and for sending a corresponding physiological signal to the transmitter 3, while the transmitter 3 receives, processes, and outputs the physiological signal to an external device 100 (see FIG. 10) for monitoring purposes.

The base 1 includes abase wall 11 that is for being adhered to the skin surface of the host via an adhesive pad 200, a groove-surrounding wall 12 that is disposed on a top surface of the base wall 11, and at least one second engaging structure 14 that is disposed on the top surface of the base wall 11. The base wall 11 has a through hole 111. The groove-surrounding wall 12 defines an installation groove 13 for the biosensor 2 to be mounted thereto.

Figure 5:
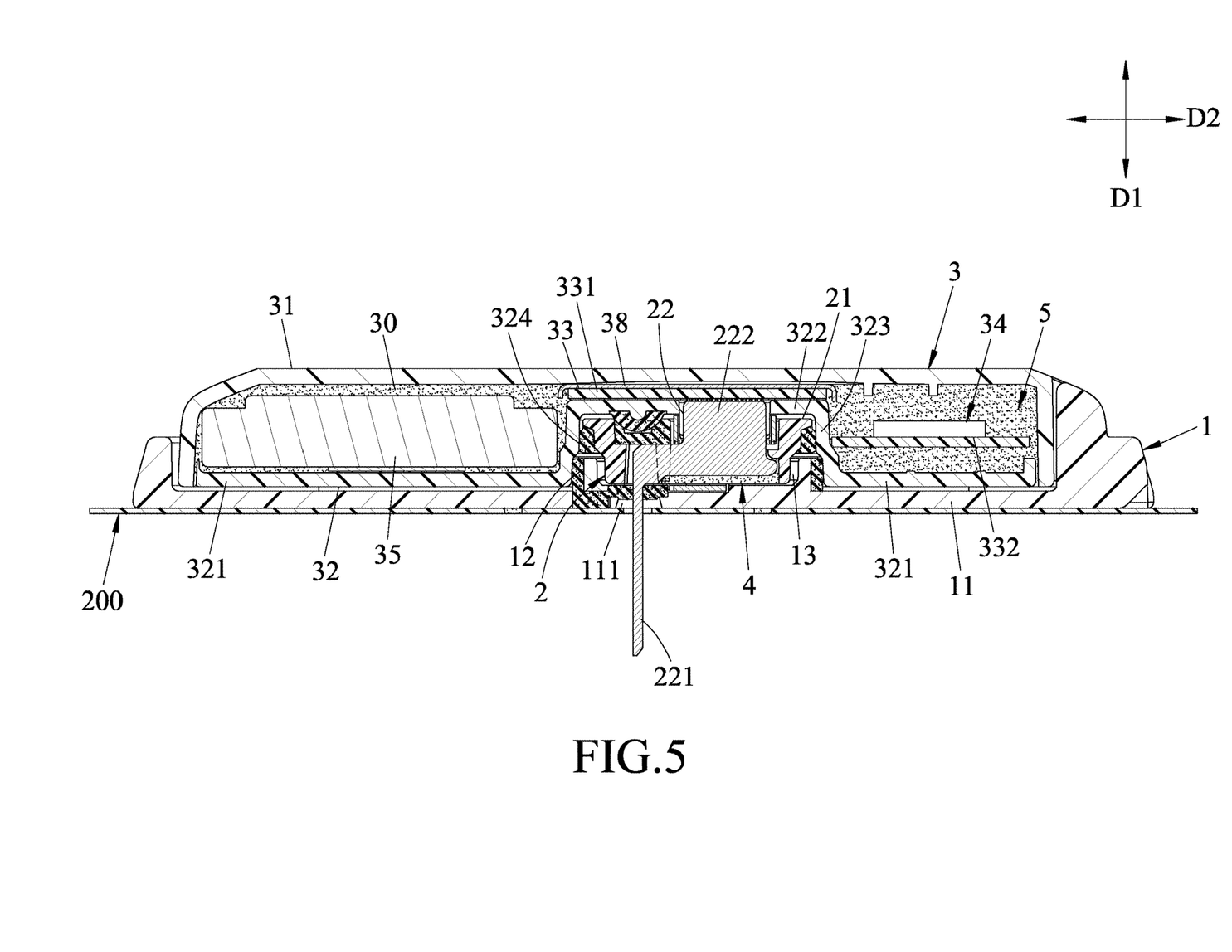
FIG. 5 is a sectional view taken along line V-V in FIG. 1.

Referring to FIGS. 2 and 5, the biosensor 2 includes a mounting seat 21 that is mounted to the installation groove 13 of the base 1, and a sensing member 22 that is carried by the mounting seat 21. The sensing member 22 has a sensing section 221 that is adapted to be inserted underneath the skin surface of the host, and a signal output section 222 that is electrically connected to the transmitter 3. The sensing section 221 extends through the through hole 111 of the base 1 to be partially inserted underneath the skin surface of the host for measuring physiological parameters related to the analyte of the host, while the signal output section 222 is adapted for sending the corresponding physiological signal to the transmitter 3 after receiving information from the sensing section 221. The sensing member 22 has a plurality of electrodes (not shown) mounted on a surface of the sensing member 22, and is covered with an analyte sensing layer (not shown). The analyte sensing layer is for reacting with the analyte of the host, and the electrodes generate an electric signal indicating the outcome of the reaction.

Figure 3:
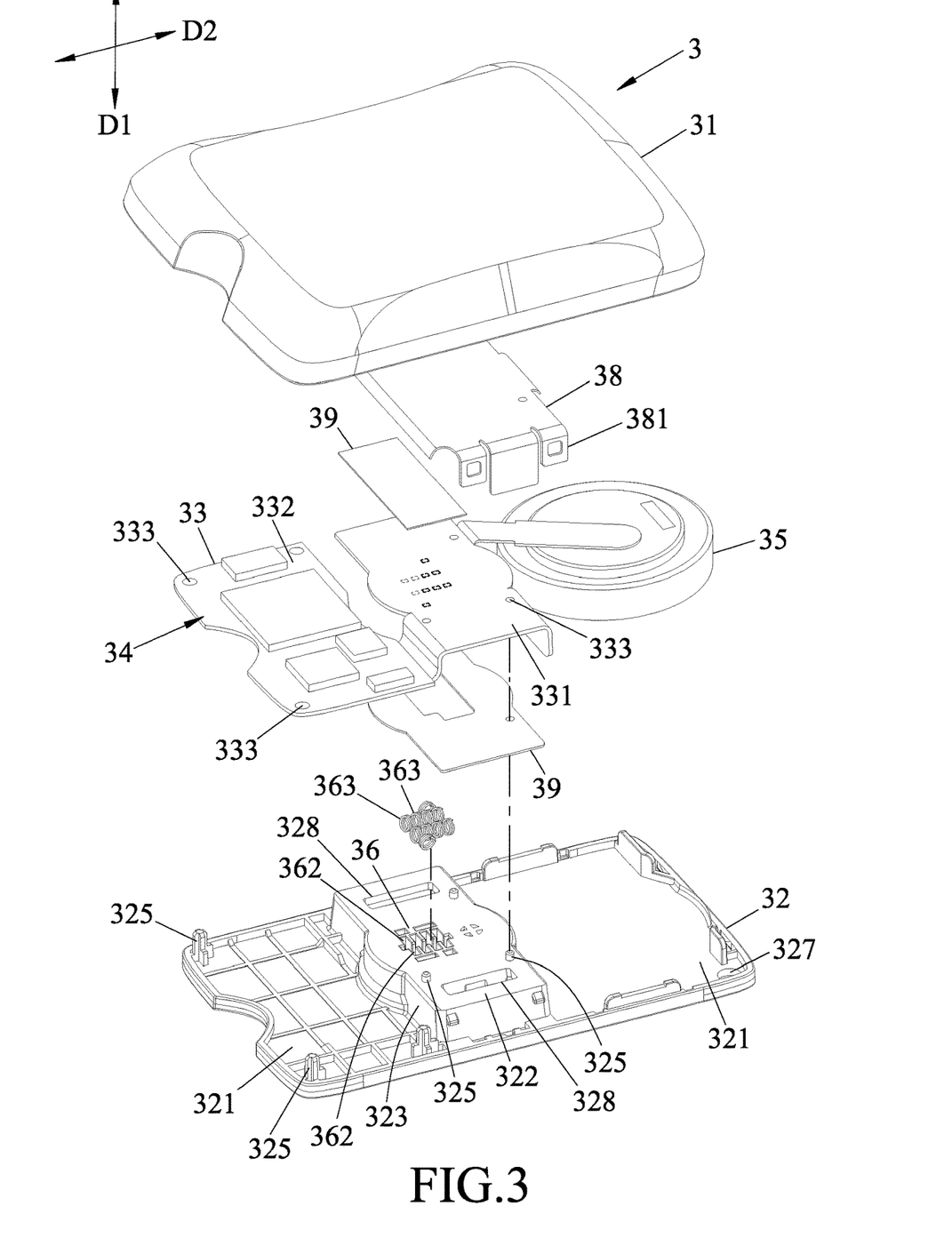
FIG. 3 is an exploded perspective view illustrating a transmitter of the first embodiment.

Referring to FIGS. 2, 3 and 5, the transmitter 3 includes a top casing 31, a bottom casing 32 that cooperates with the top casing 31 to define an inner space 30 therebetween, a circuit board 33 that is disposed in the inner space 30 and that abuts against the bottom casing 32, a processing unit 34 that is mounted to the circuit board 33, a battery 35 that is disposed in the inner space 30 and that is electrically coupled to the circuit board 33, a connecting port 36 that is disposed on the bottom casing 32 and that permits the biosensor 2 to be coupled to the circuit board 33, at least one first engaging structure 37 that is disposed on the bottom casing 32, and a support member 38 that is plate-shaped and that abuts against a top surface of the circuit board 33 and the top casing 31

In this embodiment, the top casing 31 is configured not to be formed with any through hole that extends through top and bottom surfaces thereof. With reference to FIG. 1, the transmitter 3 is mounted onto the skin surface of the host via the base 1 with the bottom casing 32 thereof facing the base 1 and with the top casing 31 thereof exposed from the base 1. As such, the top casing 31 serves to seal the bottom casing 32, and to prevent external fluid from entering the transmitter 3 to damage the electronic components in transmitter 3 via the exposed top surface of the top casing 31.

The bottom casing 32 has at least one first stepped section 321, a second stepped section 322, and a riser section 323 that interconnects the first stepped section 321 and the second stepped section 322. The second stepped section 322 is spaced apart from the first stepped section 321 in the direction of the first axis (D1) via the riser section 323. In this embodiment, the first stepped section 321 of the bottom casing 32 is distal from the top casing 31 in the direction of the first axis (D1), and the second stepped section 322 of the bottom casing 32 is proximate to the top casing 31 in the direction of the first axis (D1), such that the bottom casing 32 is formed with a first recess 324 that is located at a bottom side of the bottom casing 32, that corresponds in position to the second stepped section 322, and that is recessed toward the top casing 31 for retaining the mounting seat 21 of the biosensor 2. A depth of the first recess 324 in the direction of the first axis (D1) is no greater than a distance between a top surface of the second stepped section 322 and a bottom surface of the first stepped section 321 in the direction of the first axis (D1). Specifically, the bottom casing 32 has two first stepped sections 321 that are respectively located at two opposite sides of the second stepped section 322 in a direction of a second axis (D2) that is perpendicular to the first axis (D1). A top surface of one of the first stepped sections 321 and a top surface of the second stepped section 322 are provided with a plurality of positioning posts 325.

Figure 6:
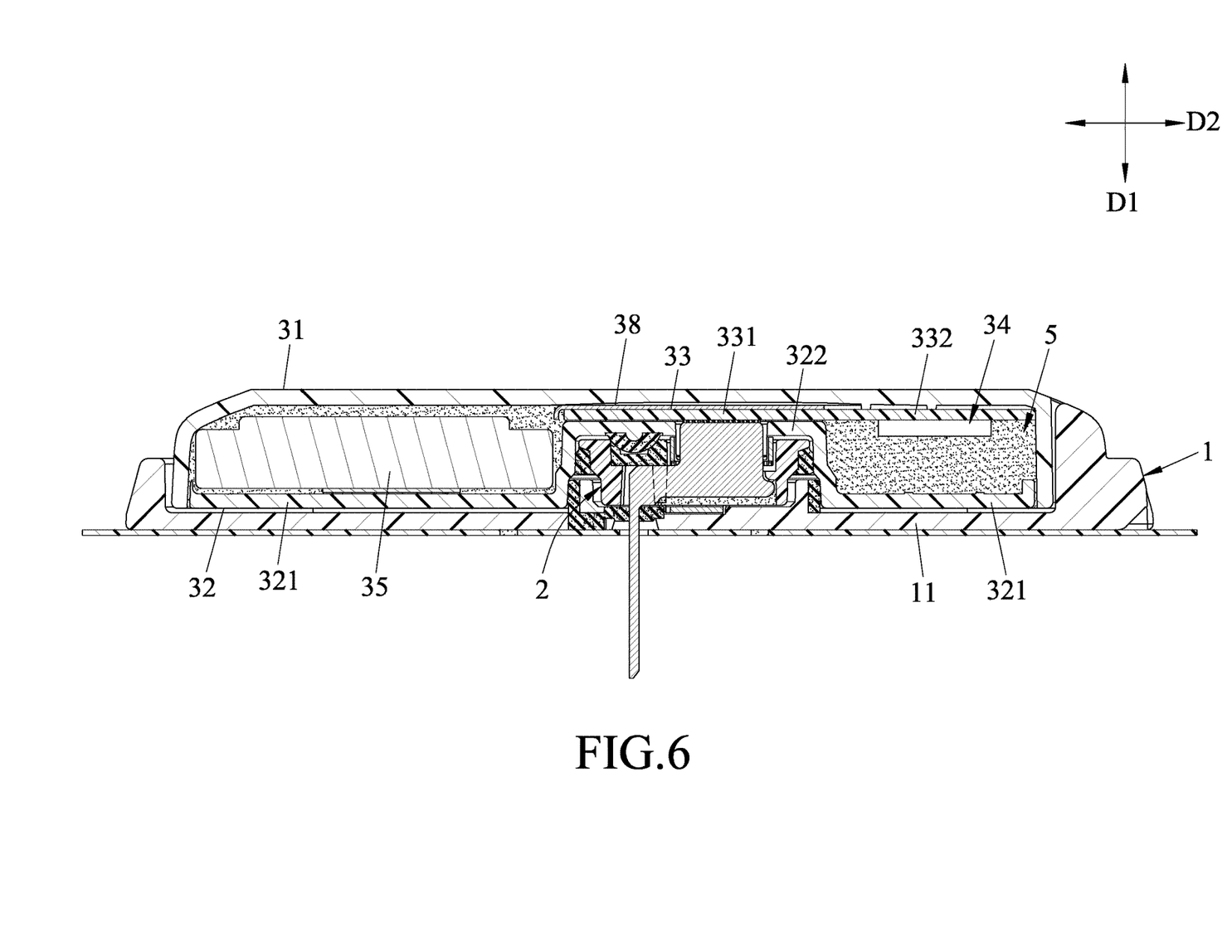
FIG. 6 is a view similar to FIG. 5 and illustrating a modification of the first embodiment.

Referring to FIGS. 3 and 5, the circuit board 33 at least abuts against the second stepped section 322, and extends toward one of the first stepped sections 321. In this embodiment, the circuit board 33 has a first board body 331 that abuts against the second stepped section 322, and a second board body 332 that is connected to the first board body 331 and that abuts against one of the first stepped sections 321. The first board body 331 and the second board body 332 are formed with a plurality of positioning holes 333 that engage with the positioning posts 325 of the bottom casing 32. The first board body 331 and the second board body 322 cooperatively form a stepped structure that extends along the second stepped section 322, the riser section 323 and the one of the first stepped sections 321. The processing unit 34 is disposed on a top surface of the second board body 322, and is located between the second board body 322 and the top casing 31. Referring to FIG. 6, in a modification, the first board body 331 and the second board body 322 of the circuit board 33' are coplanar (not forming a stepped structure), and the processing unit 34 is disposed on a bottom surface of the second board body 332 and is located between the second board body 332 and the first stepped section 321 of the bottom casing 32.

The processing unit 34 and the battery 35 correspond in position to the first stepped sections 321, and do not overlap in the direction of the first axis (D1) for reducing the thickness of the transmitter 3 along the first axis (D1). In this embodiment, the processing unit 34 corresponds in position to one of the first stepped sections 321 of the bottom casing 32, and is disposed on the second board body 332 of the circuit board 33. The battery 35 corresponds in position to the other one of the first stepped sections 321 of the bottom casing 32, and is electrically coupled to the first board body 331 of the circuit board 33. The battery 35 may not be limited to be a button cell (see FIG. 5), and may be a rechargeable battery for the transmitter 3 to be reusable.

Figure 10:
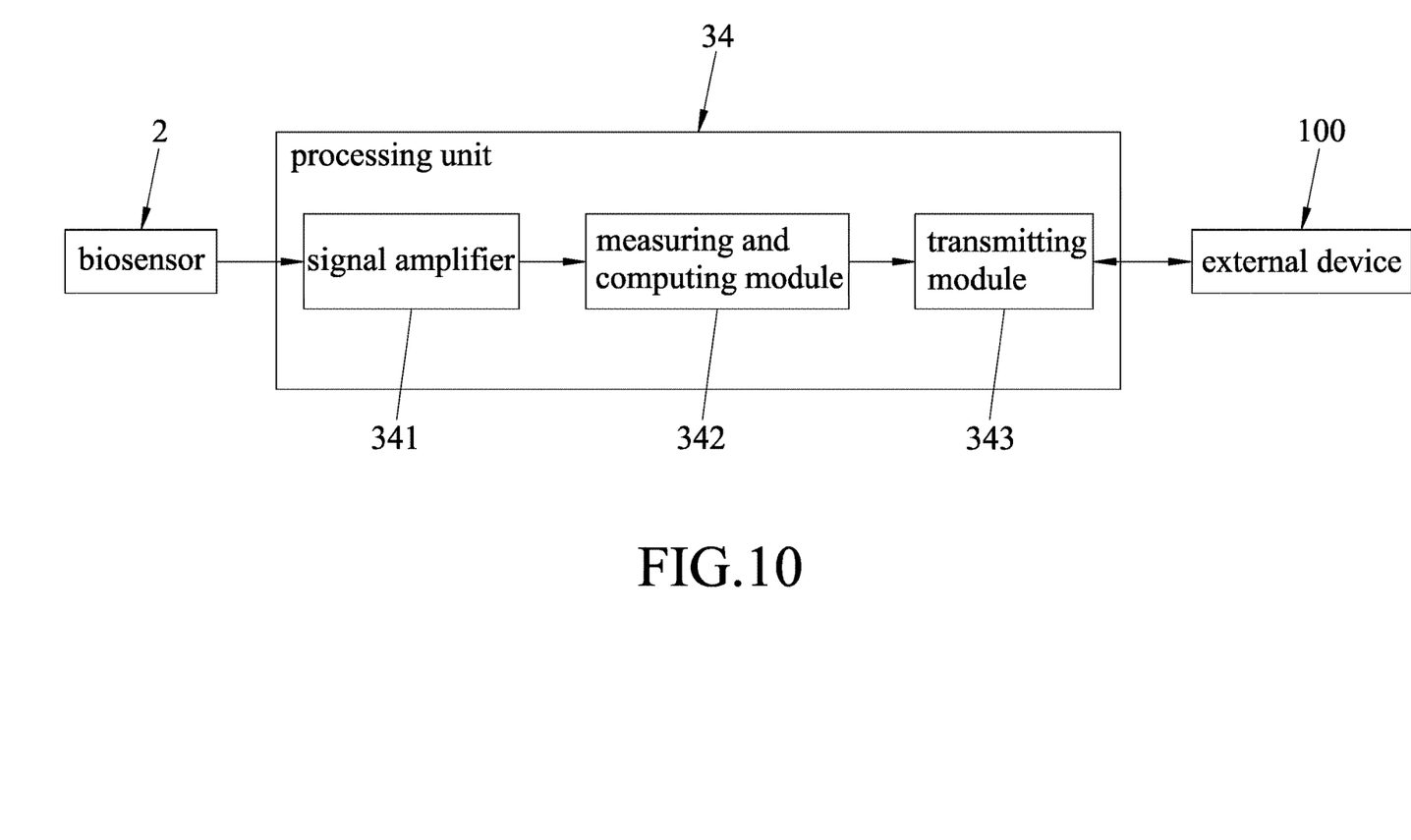
FIG. 10 is a block diagram of the embodiment.

Referring to FIG. 10, the processing unit 34 is for receiving the electric signal from the sensing member 22 and for outputting a corresponding glucose level signal. The processing unit 34 includes a signal amplifier 341 that is for receiving and amplifying the electric signal, a measuring and computing module 342 that converts the amplified electric signal sequentially into a corresponding digital signal and then to the corresponding glucose level signal, and a transmitting module 343 that sends the corresponding glucose level signal to the external device 100 via an antenna (not shown). The measuring and computing module 342 may includes an analog-digital signal converter and a processor. The transmitting module 343 may be wireless transmission means. The configuration of the processing unit 34 is not limited to the above. In this embodiment, the electric signal, the digital signal and the glucose level signal are collectively called the physiological signal.

Figure 7:
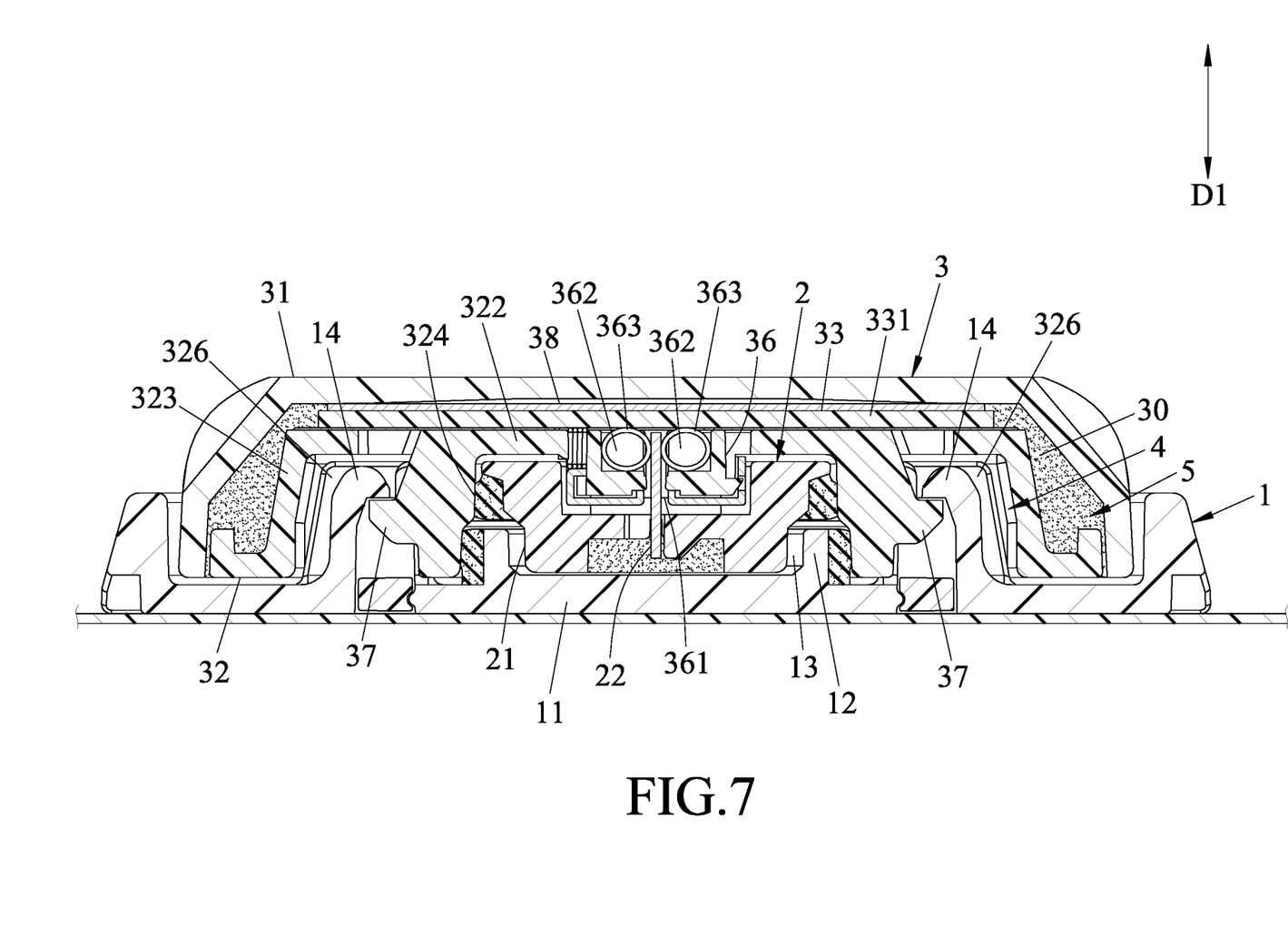
FIG. 7 is a fragmentary sectional view taken along line VII-VII in FIG. 1.

Referring to FIGS. 2, 3 and 7, the connecting port 36 is disposed on the second stepped section 322 to permit the signal output section 222 of the sensing member 22 to be coupled to the circuit board 33, so as to send the physiological signal to the processing unit 34. The connecting port 36 protrudes out from the bottom surface of the second stepped section 322 in the direction of the first axis (D1), but is configured not to protrude out from the bottom surface of the first stepped section 321. That is, the connecting port 36 is configured between the bottom surface of the second stepped section 322 and the bottom surface of the first stepped section 321. Specifically, the connecting port 36 is located in the first recess 324. The connecting port 36 has a socket 361 that opens downwardly in the direction of the first axis (D1) and that is for the sensing member 22 to be removably inserted thereinto, and a plurality of mounting grooves 362 that are formed in the top surface of the second stepped section 322 and the are laterally communicated with the socket 361. The circuit board 33 is located above the socket 361 of the connecting port 36, and is located between the biosensor 2 and the top casing 31. Each of the mounting grooves 362 receives a conductive member 363 therein that is in contact with the circuit board 33 at a top end thereof and in contact with the signal output section 222 of the sensing member 22 at a lateral end thereof for reducing the thickness of the transmitter 3 along the first axis (D1).

Figure 8:
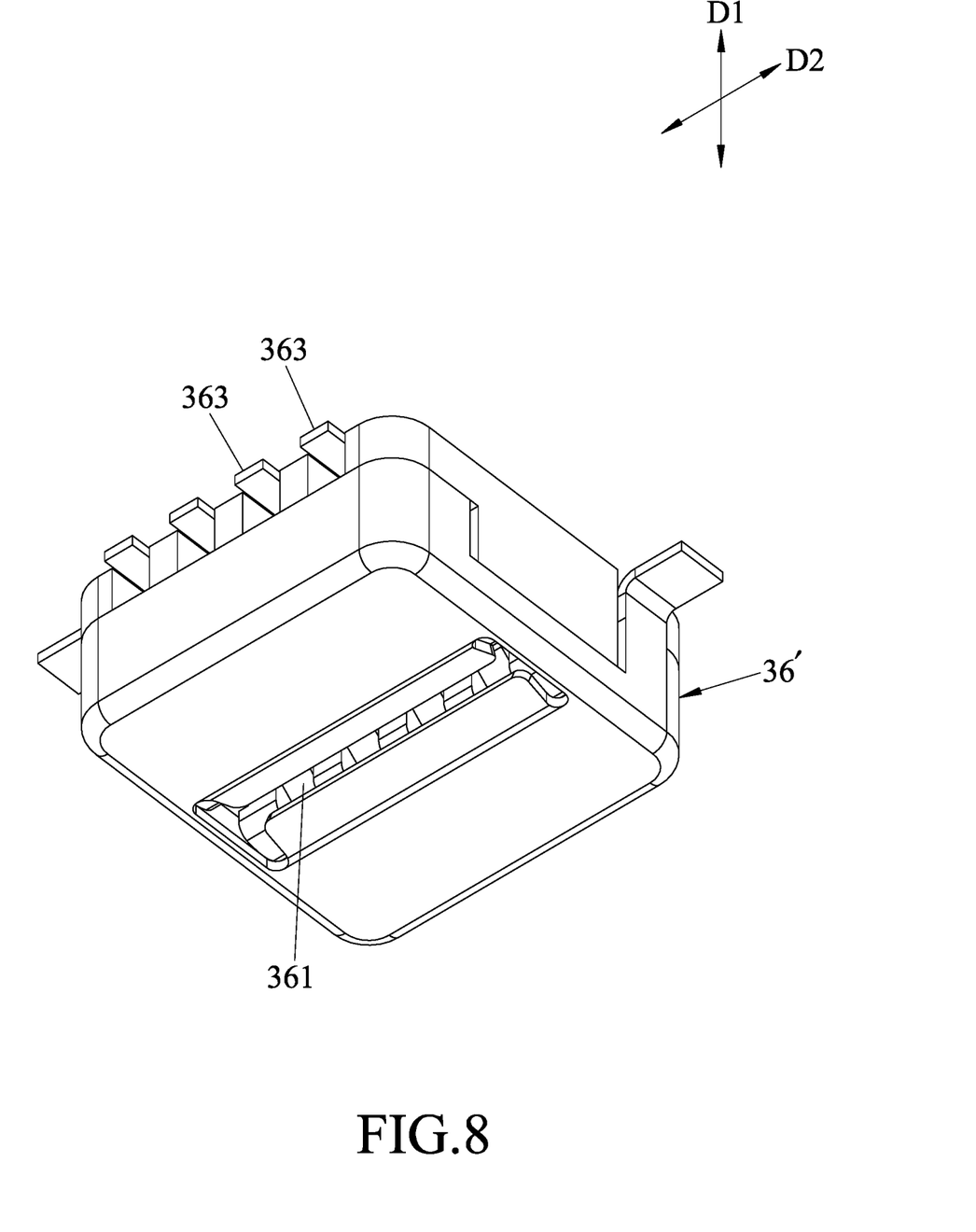
FIG. 8 is a perspective view illustrating a connecting port of a modification of the first embodiment.
Figure 9:
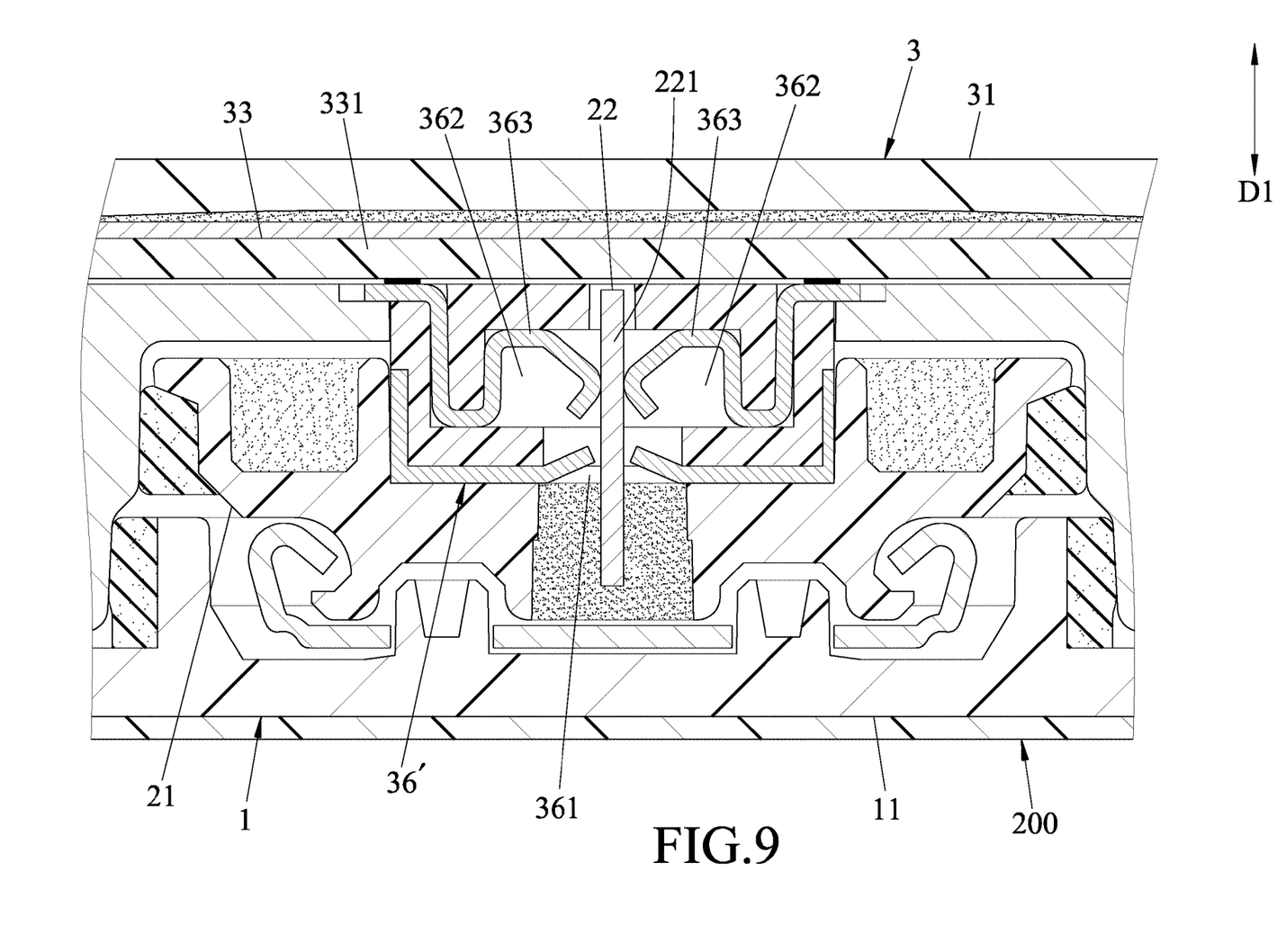
FIG. 9 is a fragmentary sectional view of the connecting port of the modification of the first embodiment in FIG. 8.

In this embodiment, the connecting port 36 and the bottom casing 32 are formed as one piece. Referring to FIGS. 8 and 9, in a modification, the connecting port 36' is in the form of an electrical connector, is disposed on the bottom surface of the first board body 331 of the circuit board 33, and extends downwardly through the bottom casing 32.

The first engaging structure 37 is configured between the bottom surface of the second stepped section 322 of the bottom casing 32 and the bottom surface of the first stepped section 321 in the direction of the first axis (D1). Referring to FIGS. 2 and 7, a bottom portion of the bottom casing 32 that corresponds in position to the second stepped section 322 is further formed with at least one second recess 326 that is recessed toward the top casing 31. The first engaging structure 37 in this embodiment is located in the second recess 326, and is configured as an engaging hook that protrudes from a recess-defining surface which defines the second recess 326. Ina modification, the first engaging structure 37 may be a groove that is formed at the recess-defining surface of the second recess 326. When the transmitter 3 is mounted to the base 1, the second engaging structure 14 at least partially engages that first engaging structure 37.

Figure 4:
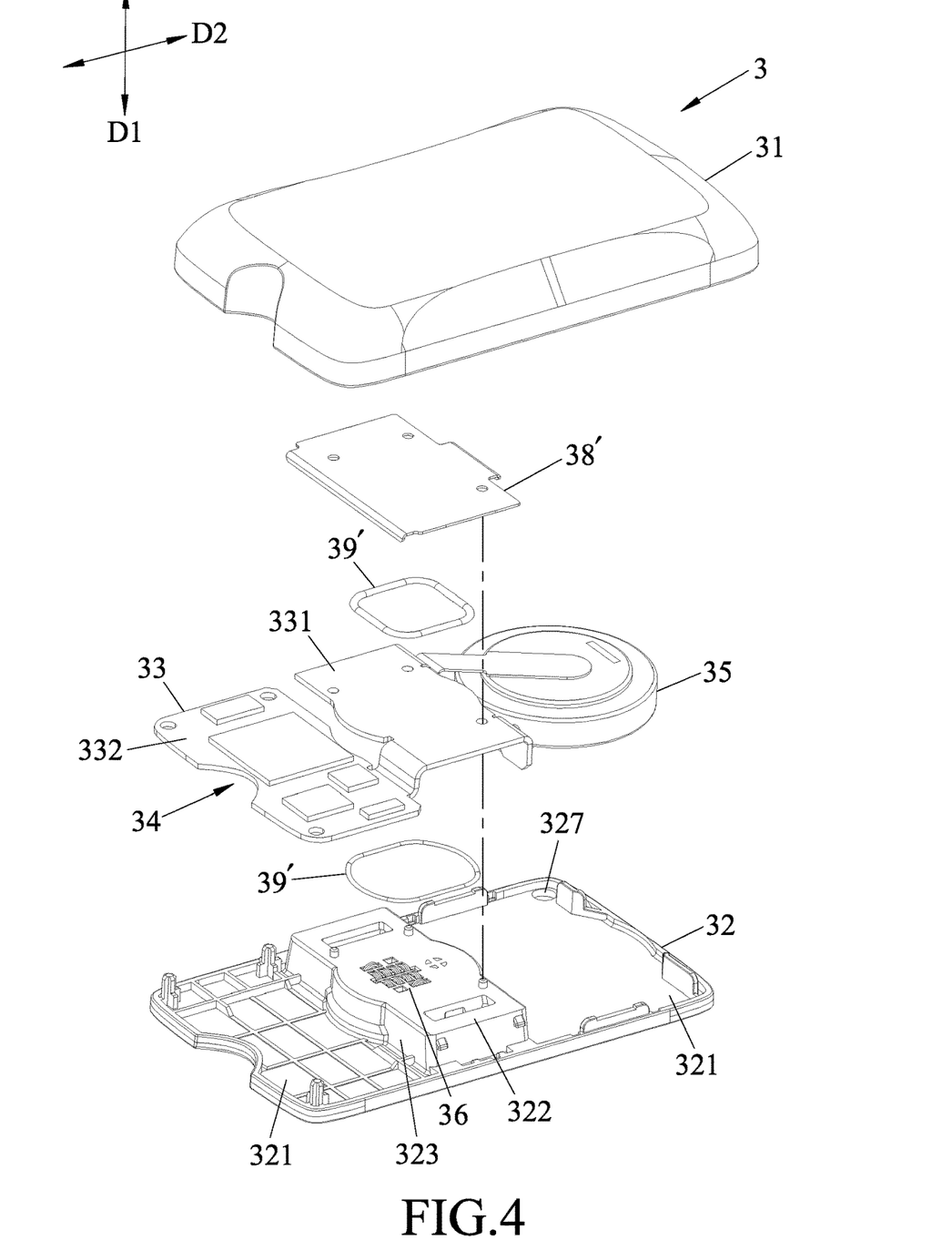
FIG. 4 is an exploded perspective view illustrating the transmitter of a modification of the first embodiment.

Referring to FIG. 3, the support member 38 serves to position the first board body 311 of the circuit board 33 relative to the bottom casing 32, to protect the circuit board 33, and to enhance the structural strength of the circuit board 33. In the embodiment, the support member 38 corresponds in position to the second stepped section 322 in the direction of the first axis (D1), and is mounted to the top surface of the circuit board 33 by an adhesive tape 39 (see FIG. 3) or a glue 39' (see FIG. 4). In addition, two opposite ends of the support member 38 extend toward the bottom casing 32 in the direction of the first axis (D1) to respectively form two engaging portions 381 (only one is visible in FIG. 3) that engage with the bottom casing 32. Referring to FIG. 4, in a modification, the support member 38' is merely adhered to the circuit board 33, and the engaging portions 381 are omitted. In another modification, the support member 33 may merely engage with the bottom casing 32, and the adhesive tape 39 or the glue 39' may be omitted.

Referring to FIG. 5, the inner space 30 of the transmitter 3 is filled with a curing agent 5 for adhering the top casing 31 and the bottom casing 32, for affixing the battery 35, the circuit board 33 and the processing unit 34, and for sealing the inner space 30. As such, the structural strength of the transmitter 3 is enhanced, and the transmitter 3 is firm, is not easily deformed, and has functions of anti-fall and anti-shock. At the same time, positioning structure and affixing structure within the transmitter 3 are simplified for facilitating use of the space in the transmitter 3. In this embodiment, the curing agent 5 is Epoxy, but may be Silicone or another material in a modification. According to the above, since the bottom casing 32 has a stepped structure, since the processing unit 34 and the battery 35 do not overlap in the direction of the first axis (D1), and since the first engaging structure 37 is configured not to protrude out from the bottom surface of the first stepped section 321, the thickness of the transmitter 3 in the direction of the first axis (D1) is reduced. Specifically, the thickness of the transmitter 3 in the direction of the first axis (D1) is less than 4 millimeters.

Referring to FIGS. 2, 5 and 7, the transmitter 3 is disposed onto the top surface of the base wall 11 of the base 1 in the direction of the first axis (D1). The first stepped section 321 of the bottom casing 32 is proximate to the base wall 11, and the second stepped section 322 is spaced apart from the base wall 11 in the direction of the first axis (D1), so as to form a layout region 4. The groove-surrounding wall 12 of the base 1 is located in the layout region 4. The first engaging structure 37 of the transmitter 3 and the second engaging structure 14 engage with each other, and are located in the layout region 4, so as to reduce a thickness of an assembly of the transmitter 3 and the base 1 in the direction of the first axis (D1) when the transmitter 3 is coupled to the base 1.

The mounting seat 21 of the biosensor 2 is received between the bottom surface of the first stepped section 321 and the bottom surface of the second stepped section 322, and the sensing section 221 of the biosensor 2 extends out of the bottom surface of the first stepped section 321 for being inserted underneath the skin surface of the host, so as to reduce a thickness of an assembly of the transmitter 3 and the biosensor 2 in the direction of the first axis (D1) when the transmitter 3 is coupled to the biosensor 2.

Since the top casing 31 is configured not to be formed with any through hole that extends through top and bottom surfaces thereof, and since the bottom casing 32 is connected to the biosensor 2 via the second stepped section 322 thereof and coupled with the base 1, sealing members merely need to be selectively disposed on the second stepped section 322, the biosensor 2 and the base 1 for preventing external fluid from entering the transmitter 3, so as to maintain the fluid-tightness of the transmitter 3.

An assembling method of the transmitter 3 of the physiological signal monitoring device according to the disclosure includes the following steps:

Step 1: placing the conductive members 363 into the mounting grooves 362 via the top surface of the bottom casing 32.

Step 2: adhering the first board body 311 of the circuit board 33 to the second stepped section 322 of the bottom casing 32 in the direction of the first axis (D1) to allow the processing unit 34 and the battery 35 that are connected to the circuit board 33 to correspond in position to the first stepped section(s) 321. In detail, step 2 can be implemented by the adhesive tape 39 or the glue 39'. Referring to FIG. 3, when the circuit board 33 is coupled to the second stepped section 322 of the bottom casing 32 by the adhesive tape 39, the adhesive tape 39 should be formed with an opening that is in communication with the connecting port 36. The adhesive tape 39 is able to seal two openings 328 of the bottom casing 32 that are for forming the first engaging structure 37 during an injection molding process of the bottom casing 32 (In FIG. 3, the openings 328 are sealed by the adhesive tape 39, but the bottom casing 32 does not necessarily have the openings 328 in a modification). Referring to FIG. 4, when the circuit board 33 is coupled to the second stepped section 322 of the bottom casing 32 by the glue 39', a moderate amount of the glue 39' is applied on the top surface of the second stepped section 322 such that the glue 39' is configured not to affect the positioning structures and the connection between the biosensor 2 and the circuit board 33 before the first board body 331 of the circuit board 33 is adhered to the second stepped section 322. In addition, after executing step 2, an external stress may be applied on the first board body 331 of the circuit board 33 to ensure the bonding strength between the circuit board 33 and the bottom casing 32.

Step 3: abutting a plate-shaped support member 38 against the first board body 331 of the circuit board 33, mounting the support member 38 to the top surface of the first board body 331 of the circuit board 33, and engaging the support member 38 with the bottom casing 32 (see FIG. 3). The support member 38 corresponds in position to the second stepped section 322 of the bottom casing 32 in the direction of the first axis (D1). Referring to FIG. 4, in a modification, the support member 38' may only be adhered to the circuit board 33. In another modification, the support member 38 may only engage with the bottom casing 32. The implementation is not limited to the abovementioned configurations. Similarly, after executing step 3, an external stress may be applied on the support member 38 to ensure the bonding strength between the support member 38 and the circuit board 33. The support member 38 may be adhered to the first board body 331 of the circuit board 33, or be combined with the circuit board through another manner before assembling the transmitter 3.

Step 4: moving the top casing 31 to face the bottom casing 32 in the direction of the first axis (D1), and coupling the top casing 31 to the bottom casing 32 such that the circuit board 33, the battery 35 and the processing unit 34 are located in the inner space 30 cooperatively defined by the top casing 31 and the bottom casing 32.

Step 5: the bottom casing 32 further has a through hole 327 that is located at one of the first stepped sections 321 and that communicates the inner space 30 with an external environment. In this step, a curing agent 5 is poured into the inner space 30 via the through hole 327. After curing of the curing agent 5, the bottom casing 32 and the top casing 31 are coupled to each other, the circuit board 33, the battery 35 and the processing unit 34 are fixedly positioned relative to each other, and the inner space 30 is sealed. Specifically, the through hole 327 is adjacent to the battery 35. In executing step 5, the transmitter 3 is vertically disposed such that the processing unit 34 is located below the battery 35, and the curing agent 5 is poured into the inner space 30 via the through hole 327 such that the curing agent 5 deposits in the inner space 30 at the location corresponding to the processing unit 34 first. At this time, if the battery 35 is desired to be reused, the deposition of the curing agent 5 may be lower than the battery 35, but is not limited to such.

By virtue of the assembling method above, the components of the transmitter 3 are assembled one after another, the inspection of the transmitter 3 is facilitated, the structural strength of the transmitter 3 is enhanced, and the positioning structure and affixing structure within the transmitter 3 are simplified so as to reduce the thickness of the transmitter 3, and to implement miniaturization of the transmitter 3.

In summary, since the bottom casing 32 has a stepped structure, the components inside and outside of the transmitter 3 may be evenly arranged, so that the thickness of the transmitter 3 in the direction of the first axis (D1) can be effectively reduced. The assembling method involves assembling the components of the transmitter 3 one after another, and affixing the components by pouring the curing agent 5. As such, the inspection of the transmitter 3 is facilitated, the positioning structure and affixing structure within the transmitter 3 are simplified, the volume of the transmitter 3 is reduced, and the fluid-tightness of the transmitter 3 is maintained.

In addition to the embodiments described above, this disclosure further discloses a plurality of embodiments as defined by the claims, with each embodiment comprising the claim elements of the respective claim and the claim elements of any claim upon which the respective claim depends.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A physiological signal monitoring device adapted for monitoring at least one physiological parameter of a host, comprising:
   a base adapted to be adhered to a skin surface of the host;
   a biosensor mounted to said base, and adapted to be partially inserted underneath the skin surface of the host for measuring and sending a physiological signal corresponding to the physiological parameter; and
   a transmitter coupled to said biosensor in a direction of a first axis, removably covering said base in the direction of the first axis, and including
      a bottom casing that has two first stepped sections, a second stepped section, and a riser section, said first stepped sections being respectively located at two opposite sides of said second stepped section in a direction of a second axis, said riser section interconnecting one of said first stepped sections and said second stepped section, said first stepped sections and said second stepped section being spaced apart from each other in the direction of the first axis, and being configured not to overlap in the direction of the first axis,
      a top casing that seals said bottom casing and that cooperates with said bottom casing to define an inner space therebetween,
      a circuit board that is located in said inner space, that at least abuts against said second stepped section, and that extends toward the one of said first stepped sections,
      a processing unit that is disposed on said circuit board and that is aligned with the one of said first stepped sections in the direction of the first axis for processing the physiological signal,
      a battery that is located in said inner space and that is electrically coupled to said circuit board, said battery being aligned with the other one of said first stepped sections in the direction of the first axis, and being configured not to overlap said processing unit in the direction of the first axis so as to reduce a thickness of said transmitter in the direction of the first axis, and
      a connecting port that is disposed on said second stepped section and that permits said biosensor to be coupled to said circuit board for sending the physiological signal to said processing unit,
   wherein a bottom portion of said bottom casing of said transmitter that is aligned with said second stepped section in the direction of the first axis is formed with a first recess for receiving said biosensor therein, said connecting port being located in said first recess,
   wherein said connecting port has a socket that opens downwardly in the direction of the first axis and that is for said biosensor to be removably inserted thereinto, and
   wherein said top casing is configured not to be formed with any through hole that extends through top and bottom surfaces thereof.

2. The physiological signal monitoring device as claimed in claim 1, wherein said first stepped sections of said bottom casing of said transmitter are distal from said top casing in the direction of the first axis, and said second stepped section of said bottom casing is proximate to said top casing in the direction of the first axis.

3. The physiological signal monitoring device as claimed in claim 2, wherein said connecting port of said transmitter protrudes out from a bottom surface of said second stepped section in the direction of the first axis, and is configured not to protrude out from bottom surfaces of said first stepped sections.

4. The physiological signal monitoring device as claimed in claim 2, wherein said connecting port further has a plurality of mounting grooves that are formed in a top surface of said second stepped section and laterally communicated with said socket, each of said mounting grooves receiving a conductive member therein, each of said conductive members being in contact with said circuit board at a top end thereof and in contact with said biosensor at a lateral end thereof.

5. The physiological signal monitoring device as claimed in claim 4, wherein said circuit board is located above said socket of said connecting port, and is located between said biosensor and said top casing.

6. The physiological signal monitoring device as claimed in claim 2, wherein a depth of said first recess in the direction of the first axis is no greater than a distance between a top surface of said second stepped section and bottom surfaces of said first stepped sections in the direction of the first axis.

7. The physiological signal monitoring device as claimed in claim 2, wherein said transmitter further has a first engaging structure for engaging said base, said first engaging structure being configured between a bottom surface of said second stepped section of said bottom casing and bottom surfaces of said first stepped sections in the direction of the first axis.

8. The physiological signal monitoring device as claimed in claim 1, wherein the thickness of said transmitter in the direction of the first axis is less than 4 millimeters.

9. The physiological signal monitoring device as claimed in claim 1, wherein said base includes a base wall, said transmitter being disposed on a top surface of said base wall in the direction of the first axis, said first stepped sections of said bottom casing being proximate to said base wall, said second stepped section being spaced apart from said base wall in the direction of the first axis, so as to form a layout region.

10. The physiological signal monitoring device as claimed in claim 9, wherein said base further includes a groove-surrounding wall that is disposed on a top surface of said base wall, said groove-surrounding wall defining an installation groove for said biosensor to be mounted thereto, said groove-surrounding wall being located in said layout region.

11. The physiological signal monitoring device as claimed in claim 10, wherein said base further includes at least one second engaging structure that is disposed on said top surface of said base wall, said transmitter further including a first engaging structure that is configured between a bottom surface of said second stepped section of said bottom casing and bottom surfaces of said first stepped sections in the direction of the first axis, said first engaging structure of said transmitter and said second engaging structure engaging with each other, and being located in said layout region.

12. The physiological signal monitoring device as claimed in claim 1, wherein the first axis is perpendicular to the second axis.

13. The physiological signal monitoring device as claimed in claim 1, wherein said inner space of said transmitter is filled with a curing agent for adhering said top casing and said bottom casing, for affixing said battery, said circuit board and said processing unit, and for sealing said inner space.

14. The physiological signal monitoring device as claimed in claim 1, wherein said circuit board has a stepped structure that extends along said second stepped section, said riser section and the one of said first stepped sections and abuts against said second stepped section and the one of said first stepped sections, said processing unit being located between said circuit board and said top casing.

15. The physiological signal monitoring device as claimed in claim 1, wherein said transmitter further includes a support member, said support member being aligned with said second stepped section in the direction of the first axis, and abutting against said top casing and a top surface of said circuit board.

16. An assembling method of the transmitter of claim 1, comprising steps of:

A) adhering a portion of the circuit board to the second stepped section of the bottom casing in the direction of the first axis to allow the processing unit and the battery that are connected to the circuit board to be aligned with the other one of the first stepped sections in the direction of the first axis;

B) moving the top casing to face the bottom casing in the direction of the first axis, and coupling the top casing to the bottom casing such that the circuit board, the battery and the processing unit are located in the inner space cooperatively defined by the top casing and the bottom casing; and C) the bottom casing further having a through hole that communicates the inner space with an external environment, pouring a curing agent into the inner space via the through hole of the bottom casing such that the bottom casing and the top casing are coupled to each other, that the circuit board, the battery and the processing unit are fixedly positioned relative to each other, and that the inner space is sealed.

17. The assembling method as claimed in claim 16, wherein the through hole is located at the other one of the first stepped sections and is adjacent to the battery, in executing step C), the transmitter being vertically disposed before the curing agent is poured into the inner space so as to locate the processing unit below the battery, such that curing agent deposits in the inner space at a location corresponding to the processing unit first.

18. The assembling method as claimed in claim 17, further comprising, between step A) and step B), a step of A') placing a support member to be aligned with the second stepped section of the bottom casing in the direction of the first axis, and mounting the support member to a top surface of the circuit board.

\* \* \* \* \*